United States Patent
Forghanian-Arani et al.

(10) Patent No.: US 12,130,348 B2
(45) Date of Patent: Oct. 29, 2024

(54) CONTINUOUS THREE-DIMENSIONAL IMAGING FOR MAGNETIC RESONANCE ELASTOGRAPHY

(71) Applicant: Mayo Foundation for Medical Education and Research, Rochester, MN (US)

(72) Inventors: Arvin Forghanian-Arani, Rochester, MN (US); Joshua D. Trzasko, Rochester, MN (US); Yi Sui, Rochester, MN (US); Philip A. Araoz, Rochester, MN (US); Richard L. Ehman, Rochester, MN (US); John Huston, III, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 111 days.

(21) Appl. No.: 17/793,633

(22) PCT Filed: Jan. 15, 2021

(86) PCT No.: PCT/US2021/013574
§ 371 (c)(1),
(2) Date: Jul. 18, 2022

(87) PCT Pub. No.: WO2021/146519
PCT Pub. Date: Jul. 22, 2021

(65) Prior Publication Data
US 2023/0061571 A1    Mar. 2, 2023

Related U.S. Application Data

(60) Provisional application No. 62/962,029, filed on Jan. 16, 2020, provisional application No. 62/966,007, filed on Jan. 26, 2020.

(51) Int. Cl.
*G01R 33/563*    (2006.01)
*A61B 5/00*    (2006.01)
(Continued)

(52) U.S. Cl.
CPC ...... *G01R 33/56375* (2013.01); *A61B 5/0051* (2013.01); *A61B 5/055* (2013.01);
(Continued)

(58) Field of Classification Search
CPC .................. A61B 5/055; A61B 5/0051; G01R 33/56545; G01R 33/56375;
(Continued)

(56) References Cited

U.S. PATENT DOCUMENTS 7,259,557 B2    8/2007  Hinks et al.
9,805,481 B2 *  10/2017 Sperl ..................... G06T 11/006
(Continued)

FOREIGN PATENT DOCUMENTS

WO    2021146519 A1    7/2021

OTHER PUBLICATIONS

International Search Report of related PCT/US2021/013574, mailed on Apr. 19, 2021, 3 pages.
(Continued)

*Primary Examiner* — Baisakhi Roy
(74) *Attorney, Agent, or Firm* — Quarles & Brady LLP (57) ABSTRACT

Described here are systems and methods for a robust magnetic resonance elastography ("MRE") imaging platform for rapid dynamic 3D MRE imaging. The imaging platform includes an MRE pulse sequence and advanced image reconstruction framework that work synergistically in order to greatly expand the domains where MRE can be deployed successfully.

13 Claims, 4 Drawing Sheets

(51) Int. Cl.
  *A61B 5/055*  (2006.01)
  *G01R 33/48* (2006.01)
  *G06T 11/00* (2006.01)

(52) U.S. Cl.
  CPC ...  *G01R 33/4818* (2013.01); *G01R 33/56358* (2013.01); *G06T 11/003* (2013.01); *A61B 5/0044* (2013.01); *G06T 2210/41* (2013.01)

(58) Field of Classification Search
  CPC ............ G01R 33/4818; G01R 33/5601; G01R 33/5611; G01R 33/5608; G01R 33/5616; G01R 33/385; G01R 33/565638
  See application file for complete search history.

(56) References Cited

U.S. PATENT DOCUMENTS

| | | | | |
|---|---|---|---|---|
| 10,317,496 | B2* | 6/2019 | Choi | G01R 33/5611 |
| 10,463,331 | B2* | 11/2019 | Goshen | A61B 6/5205 |
| 2011/0044524 | A1* | 2/2011 | Wang | G01R 33/5601 |
| | | | | 382/131 |
| 2011/0282181 | A1* | 11/2011 | Wang | A61B 5/0095 |
| | | | | 600/407 |
| 2012/0099774 | A1* | 4/2012 | Akcakaya | G06T 11/008 |
| | | | | 382/131 |
| 2013/0088225 | A1* | 4/2013 | Weller | G01R 33/5611 |
| | | | | 324/322 |
| 2015/0086131 | A1* | 3/2015 | Wang | G06T 5/73 |
| | | | | 382/275 |
| 2015/0285889 | A1* | 10/2015 | Chen | A61B 5/0044 |
| | | | | 324/309 |
| 2015/0309136 | A1* | 10/2015 | Shu | G01R 33/5611 |
| | | | | 324/309 |
| 2015/0309145 | A1* | 10/2015 | Klatt | G01R 33/385 |
| | | | | 324/309 |
| 2016/0266225 | A1* | 9/2016 | Johnson | G01R 33/56545 |
| 2017/0307714 | A1* | 10/2017 | Okell | G01R 33/56366 |
| 2018/0203088 | A1* | 7/2018 | Tao | G01R 33/56563 |
| 2018/0247436 | A1* | 8/2018 | Korobchenko | G06T 11/005 |
| 2019/0011522 | A1* | 1/2019 | Yin | A61B 5/055 |
| 2019/0355125 | A1* | 11/2019 | Park | G06T 7/174 |
| 2020/0072928 | A1* | 3/2020 | Patil | G01R 33/5616 |
| 2020/0225307 | A1* | 7/2020 | Otazo | G01R 33/5611 |
| 2021/0116528 | A1* | 4/2021 | Kopanoglu | G01R 33/5608 |

OTHER PUBLICATIONS

Written Opinion of related PCT/2021/013574, mailed on Apr. 19, 2021, 9 pages.
Baker, Christopher A., et al. "Translational-invariant dictionaries for compressed sensing in magnetic resonance imaging." 2011 IEEE International Symposium on Biomedical Imaging: From Nano to Macro. IEEE, 2011.
Bernstein, Matt A., et al. "Reconstructions of phase contrast, phased array multicoil data." Magnetic resonance in medicine 32.3 (1994): 330-334.
Feng, Li, et al. "XD-GRASP: golden-angle radial MRI with reconstruction of extra motion-state dimensions using compressed sensing." Magnetic resonance in medicine 75.2 (2016): 775-788.
Hao, Wangli, et al. "Fast iterative contourlet thresholding for compressed sensing MRI." Electronics Letters 49.19 (2013): 1206-1208.
Pipe, J. G., & Menon, P. (1999). Sampling density compensation in MRI: rationale and an iterative numerical solution. Magnetic Resonance in Medicine: An Official Journal of the International Society for Magnetic Resonance in Medicine, 41(1), 179-186.
Rump, Jens, et al. "Fractional encoding of harmonic motions in MR elastography." Magnetic Resonance in Medicine: An Official Journal of the International Society for Magnetic Resonance in Medicine 57.2 (2007): 388-395.
Sui, Yi, et al. "Turbine-MRE: a 3D hybrid radial-Cartesian EPI acquisition for MR elastography." Magnetic resonance in medicine 85.2 (2021): 945-952.
Zaitsev, M., J. Hennig, and O. Speck. "Point spread function mapping with parallel imaging techniques and high acceleration factors: Fast, robust, and flexible method for echo-planar imaging distortion correction." Magnetic Resonance in Medicine: An Official Journal of the International Society for Magnetic Resonance in Medicine 52.5 (2004): 1156-1166.
Pepin, K., et al. "Perfusion MRI and MRE for Sarcomas: A novel imaging quest for surgical planning, radiation therapy planning and treatment response assessment." Mayo Clinic (2016); pp. 1-33.
Ebersole, C., et al., A Bayesian Method for Accelerated Magnetic Resonance Elastography of the Liver, Magn Reson Med. (2018);80(3):1178-1188. doi:10.1002/mrm.27083.
Pepin, K. et al., MR Elastography and Perfusion MRI for the Early Assessment of Treatment Response in Soft Tissue Sarcomas. ISMRM 2017 (International Society for Magnetic Resonance in Medicine); pp. 1-4.
Glaser, K. J., Manduca, A., & Ehman, R. L. (2012). Review of MR elastography applications and recent developments. Journal of magnetic resonance imaging : JMRI, 36(4), 757-774. https://doi.org/10.1002/jmri.23597.
Bruder, H., et al. "Image reconstruction for echo planar imaging with nonequidistant k-space sampling." Magnetic resonance in medicine 23.2 (1992): 311-323.
Fessler, Jeffrey A., and Bradley P. Sutton. "Nonuniform fast Fourier transforms using min-max interpolation." IEEE transactions on signal processing 51.2 (2003): 560-574.
Kazerouni, Abbas, et al. "Bayesian denoising: From MAP to MMSE using consistent cycle spinning." IEEE Signal Processing Letters 20.3 (2013): 249-252.
Huang, Junzhou, Shaoting Zhang, and Dimitris Metaxas. "Efficient MR image reconstruction for compressed MR imaging." Medical Image Analysis 15.5 (2011): 670-679.
Murphy, Matthew C., et al. "Measuring the characteristic topography of brain stiffness with magnetic resonance elastography." PloS one 8.12 (2013): e81668.
Pruessmann, K. P., Weiger, M., Bornert, P., & Boesiger, P. (2001). Advances in sensitivity encoding with arbitrary k-space trajectories. Magnetic resonance in medicine, 46(4), 638-651. https://doi.org/10.1002/mrm.1241.
Sui, Yi, et al. "Turbine-MRE: a 3D Hybrid Radial-Cartesian EPI Acquisition for MR Elastography", Proceedings of the International Society for Magnetic Resonance in Medicine, 26th Annual Meeting and Exhibition, Paris, France, Jun. 16-21, 2018, vol. 26, 5581, Jun. 1, 2018.

* cited by examiner

CONTINUOUS THREE-DIMENSIONAL IMAGING FOR MAGNETIC RESONANCE ELASTOGRAPHY

CROSS-REFERENCE TO RELATED APPLICATIONS

This application represents the national stage entry of PCT/US2021/013574 filed on Jun. 15, 2021 and claims the benefit of U.S. Provisional Patent Application Ser. No. 62/962,029 filed on Jan. 16, 2020 and entitled "A Continuous 3D Imaging Strategy for Magnetic Resonance Elastography," and U.S. Provisional Patent Application Ser. No. 62/966,007 filed on Jan. 26, 2020 and entitled "Continuous Three-Dimensional Imaging for Magnetic Resonance Elastography," which are incorporated herein by reference as if set forth in their entirety for all purposes.

STATEMENT REGARDING FEDERALLY SPONSORED RESEARCH

This invention was made with government support under EB001981 awarded by the National Institutes of Health. The government has certain rights in the invention.

BACKGROUND

Magnetic resonance elastography ("MRE") is a phase contrast magnetic resonance imaging ("MRI") technique for quantitatively measuring tissue stiffness. Clinically, MRE has primarily been applied to diagnosing and staging liver fibrosis, but is actively being researched for other anatomical regions, including neuro, breast, and prostate. Recently, investigations into the dynamic nature of tissue stiffness with applications such as functional brain MRE, muscle activation during exercise, and cardiac imaging are underway.

MRE exams have historically focused on static anatomical targets, and in turn generated static displays of tissues stiffness information. However, anatomical targets of interest are often changing dynamically, either due to bulk tissue motion (voluntary or involuntary) or from physiological changes occurring in the target anatomy. Examples of the former include muscle activation during exercise and cardiac imaging, while the latter includes functional applications (i.e., functional elastography). In the former case, dynamic MRE capabilities may be desired to create dynamic stiffness maps that are either absent of patient motion artifacts or reflect stiffness changes in response to deformation, such as cardiac strain. In the latter, dynamic stiffness maps may be of interest to investigate correlative changes with other physiological processes, such as response to neural activity.

There remains a need to generate MRE images exhibiting high spatial resolution, and temporal resolution, to meet the needs of applications such as dynamic stiffness maps. Accelerated imaging strategies will be paramount to the success of the latter investigations.

SUMMARY OF THE DISCLOSURE

The present disclosure addresses the aforementioned drawbacks by providing a method for generating a mechanical property map using a magnetic resonance imaging (MRI) system. The method includes acquiring data from a subject using the MRI system while a vibratory stimulus is provided to the subject in order to induce motion within a tissue of the subject. The data may be acquired using a pulse sequence that samples k-space in a plurality of planes using an echo planar readout, where each plane is radially rotated about a phase encoding axis in successive repetition time periods of the pulse sequence. The pulse sequence also includes motion encoding gradients that are generated before each echo planar readout in order to encode the motion within the tissue into an image phase of the data. A plurality of images may be reconstructed from the data using an iterative image reconstruction technique. The reconstructed images are indicative of the image phase into which the motion within the tissue has been encoded. A mechanical property map may then be generated from the reconstructed images.

In one aspect, a method is provided for generating a mechanical property map using a magnetic resonance imaging (MRI) system. The method includes acquiring data from a subject using the MRI system while a vibratory stimulus is provided to the subject in order to induce motion within a tissue of the subject. The data are acquired using a pulse sequence that samples k-space in a plurality of planes using an echo planar readout, each plane is radially rotated about a phase encoding axis in successive repetition time periods of the pulse sequence, and the pulse sequence includes motion encoding gradients that are generated before each echo planar readout in order to encode the motion within the tissue into an image phase of the data. The method also includes reconstructing a plurality of images from the data using an iterative image reconstruction technique. The reconstructed images are indicative of the image phase into which the motion within the tissue has been encoded. The method also includes generating a mechanical property map from the reconstructed images.

In one aspect, a magnetic resonance imaging (MRI) system is provided for generating a mechanical property map of a subject. The system includes a vibratory stimulus system configured to induce motion within a tissue of the subject. The system also includes a computer system configured to: i) acquire data from the subject, while the induced motion is provided to the subject, using a pulse sequence that samples k-space in a plurality of planes using an echo planar readout; ii) radially rotate each plane about a phase encoding axis in successive repetition time periods of the pulse sequence that includes motion encoding gradients that are generated before each echo planar readout in order to encode the motion within the tissue into an image phase of the data; iii) reconstruct a plurality of images, which are indicative of the image phase into which the motion within the tissue has been encoded, from the data using an iterative image reconstruction technique; and iv) generate a mechanical property map from the reconstructed images.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for a robust magnetic resonance elastography ("MRE") imaging platform for rapid dynamic 3D MRE imaging. The imaging platform includes an MRE pulse sequence and advanced image reconstruction framework that work synergistically in order to greatly expand the domains where MRE can be deployed successfully.

Figure 1:
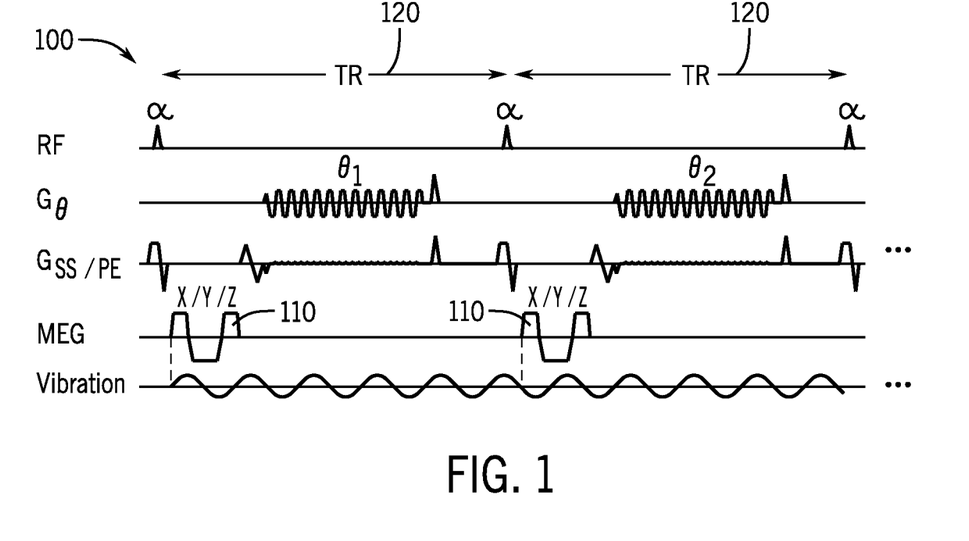
FIG. 1 is a pulse sequence diagram illustrating a non-limiting example pulse sequence for acquiring MRE data according to some embodiments described in the present disclosure.

Referring to FIG. 1, a non-limiting example pulse sequence 100 for use in accordance with the present disclosure is shown. The systems and methods described in the present disclosure may use a pulse sequence that is adapted from a 3D hybrid radial-Cartesian readout scheme referred to as "Trajectory Using Radially Batched Internal Navigator Echoes ("TURBINE"). As shown in FIG. 1, the adapted pulse sequence 100 described in the present disclosure is based on a spoiled gradient-echo MRE sequence with a modified echo-planar imaging ("EPI") readout.

In the pulse sequence, the EPI readout plane is rotated radially about the phase-encoding (GPE) axis in successive repetition times ("TRs") 120 to sample a full 3D k-space volume. MRE motion-encoding gradients ("MEGs") 110 are added prior to the EPI readout to encode MRE harmonic tissue motion into the image phase, and can be applied on the x, y, and/or z-axes to record the full harmonic displacement field. The triggering of the mechanical vibration can be temporally shifted with respect to the MEGs 110 by a time delay (cp) in each acquisition to acquire wave images at different phases of the harmonic motion.

To implement the TURBINE acquisition, the EPI readout axis, Go, is rotated about the slab-selective (Gss)/phase-encoding (GPE) axis in successive TRs 120. One 2D plane within the target 3D k-space can be sampled with the EPI trajectory (which may be referred to as a TURBINE blade) during each TR 120.

Figure 2:
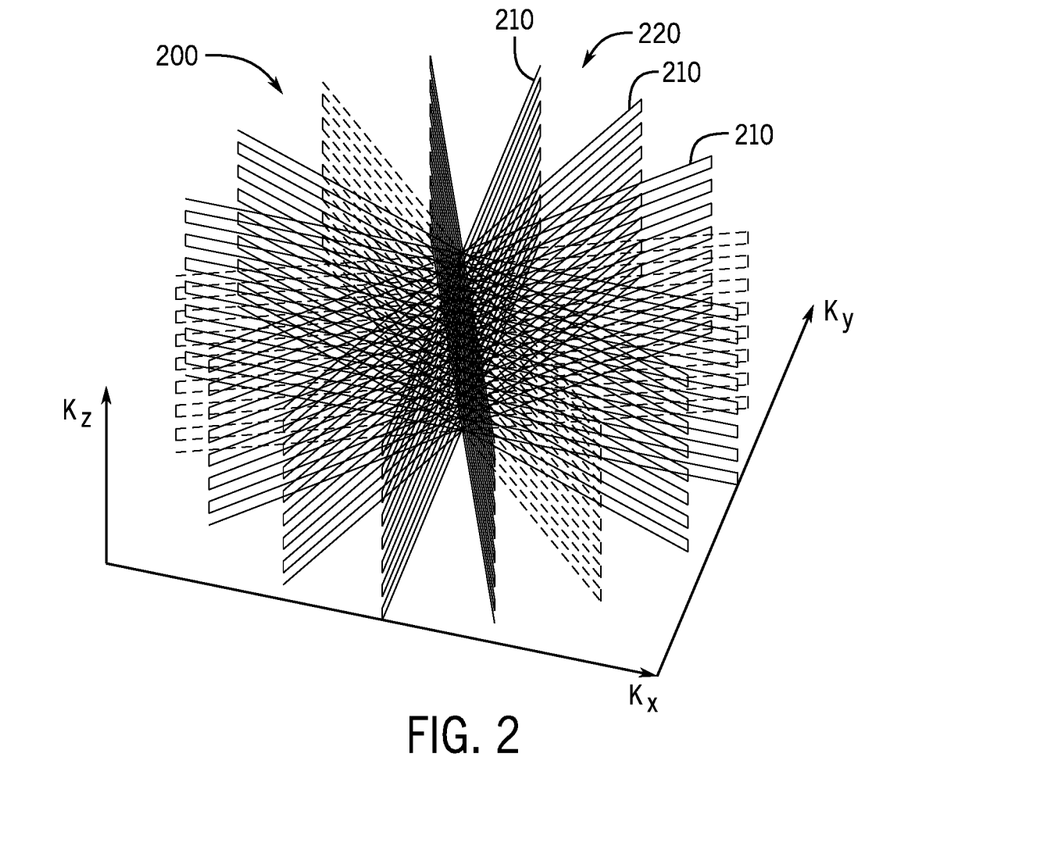
FIG. 2 illustrates a sampling of k-space using the pulse sequence diagram of FIG. 1.

Referring to FIG. 2, a non-limiting example of the k-space sampling 200 achieved with a TURBINE-MRE acquisition is shown. To cover all of 3D k-space, the sampling plane 210 can be angularly rotated by a fixed increment 220 before each repetition. The angular sampling can be evenly distributed over 180 degrees, distributed with a golden angle increment, or distributed in other manners, which may include random or pseudorandom increments.

In some implementations, a sampling plane 210 may be an EPI blade for an EPI sequence. Non-phase encoded reference data (e.g., k-space lines) may be acquired prior to actual scan data for each EPI blade at the same radial angles.

Figure 3:
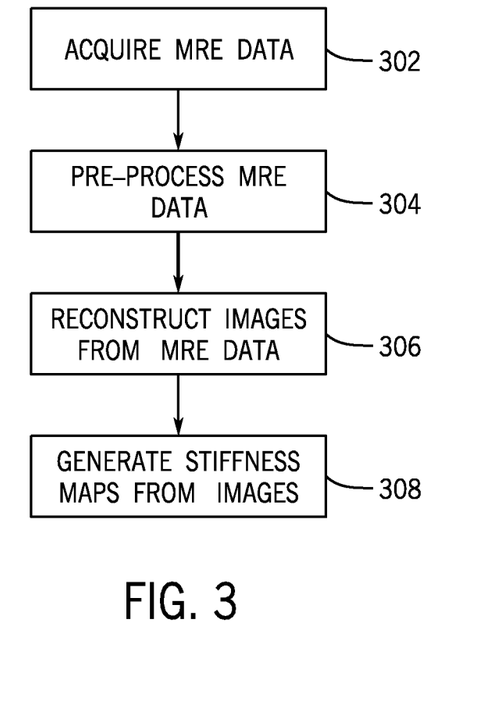
FIG. 3 is a flowchart setting forth the steps of a non-limiting example method for generating a mechanical property map (e.g., a stiffness map) using the pulse sequences described in the present disclosure.

Referring now to FIG. 3, a flowchart is illustrated as setting forth the steps for a non-limiting example method for acquiring MRE data using a TURBINE-MRE pulse sequence, such as the one shown in FIG. 1, and generating therefrom images, which may include tissue stiffness or other mechanical property maps.

The non-limiting example method includes acquiring data with an MRI system using the described TURBINE-MRE pulse sequence, as indicated at step 302. In an example study, a polyvinyl chloride ("PVC") phantom and 6 volunteers were scanned on a compact 3T scanner with a 32-channel head coil at 80 Hz and 60 Hz external vibration. 192 radial-encoding positions were scanned with golden angle increment. A complete MRE dataset with 6 motion-encoding directions ($\pm X$, $\pm Y$, and $\pm Z$) and 4 time offsets were acquired within 4 minutes. In some implementations, the MRE acquisition can be accelerated by undersampling in k-space.

After the MRE data are acquired, they may be optionally pre-processed before reconstruction, as indicated at step 304. In non-limiting examples, one-dimensional zero and first-order phase correction can be applied before variable readout gradient filtering (VRGF) resampling on every EPI blade to minimize Nyquist ghosts.

One or more images may then be reconstructed from the MRE data, as indicated at step 306. In some configurations, the images may be reconstructed using an iterative image reconstruction. In a non-limiting example, a Tikhonov-regularized SENSE (e.g., linear least squares with quadratic regularization) reconstruction of the MRE data can be performed. Images can be reconstructed from multi-coil 3D radial-Cartesian TURBINE-MRE data using a Tikhonov-regularized SENSE reconstruction performed via conjugate-gradient iteration. The number of iterations can be fixed, such as fixed at 40. In some implementations of such a reconstruction algorithm, the discrete-space Fourier Transform ("DSFT") operations implicit within the SENSE acquisition model can be executed using the non-uniform FFT ("NUFFT"). Coil sensitivity profiles can be estimated from a separate calibration scan using a gradient echo sequence, or using other techniques known in the art. In some configurations, the Tikhonov regularization parameter can be, for example, manually selected (e.g., using a value of $\lambda=0.001$).

As another non-limiting example, images can be reconstructed using a sparsity regularized iterative reconstruction, such as a sparsity regularized least squares estimation. This reconstruction can be based on a signal model, such as an affine signal model, $g=Af+n$; where g is the acquired data; A is a TURBINE forward operator, which include coils sensitivity encoding, in plane radial Fourier encoding (e.g., via the non-uniform FFT (NUFFT)), and through-plane uniform undersampling; f is the target signal; and n is noise, such as zero-mean complex Gaussian noise. As one non-limiting example, a sparsity regularized reconstruction can implement L1-regularization with a lifted Daubechies-4 wavelet transform and 5×5-neighborhood cycle spinning. In one example implementation, the reconstruction was performed via a Fast Composite Splitting Algorithm ("FCSA"), with iter=200 for a 32-blade data set and iter=300 for a 16-blade data set. Regularization parameters can be manually tuned for each setup.

MRE stiffness maps can be generated from the reconstructed images, as indicated at step 308. As one non-limiting example, the MRE stiffness maps can be generated by adaptively taking the curl of the 3D displacement (indicative from the reconstructed images), smoothing the curl images, and performing a 3D direct inversion ("DI") algorithm to invert the wave-field.

In one non-limiting example, the TURBINE acquisition scheme was implemented together with MRE motion encoding. The phase difference images were successfully reconstructed to obtain the wave displacement information.

Using the systems and methods described in the present disclosure, MRE data can be acquired from large imaging volumes with high spatial resolution in clinically acceptable times. For example, whole brain volume data with a high spatial resolution (e.g., 2.5 mm isotropic) can be collected within four minutes.

The radial sampling scheme of the TURBINE-MRE pulse sequence described in the present disclosure, together with a suitable iterative reconstruction, may enable accelerated acquisitions while still maintaining accurate stiffness estimation. As a non-limiting example, as few as 64 blades (which in one example were collected in a 1 minute 20 seconds scan) can be sufficient for a consistent stiffness measurement. In implementations where a joint nonlinear regularization model is implemented within the reconstruction, a comparable reconstruction accuracy can be obtained from even fewer acquired blades, further reducing overall scan time.

The TURBINE-MRE pulse sequences described in the present disclosure may be self-navigating and may therefore be highly accelerated to be suitable for imaging moving objects. Such applications are particularly beneficial for cardiac MRE applications, which are currently performed with 2D EPI-based acquisitions and face additional challenges due to the simultaneous presence of cardiac and respiratory motion. Conventional EPI-MRE sequences acquire only one cardiac phase within a breath-hold, which is inefficient to collect data for multiple cardiac phases. The breath-hold (typically 15-20 sec) may also impose difficulties for some cardiac patients. The TURBINE-MRE sequences described in the present disclosure provide a foundation upon which a free-breathing, cinematic-type, MRE acquisition can be built. For instance, cardiac MRE can be realized using a continuous golden-angle rotation scheme with the TURBINE-MRE pulse sequence, retrospective cardiac and respiratory binning of k-space data in discrete motion states, and compressed sensing reconstruction similar to XD-GRASP.

In some aspects, a relative long echo time in TURBINE-MRE sequence due to the presence of MEGs may make it prone to susceptibility artifacts and signal drop-out at regions of high susceptibility variation, such as the orbitofrontal and temporomesial brain areas. To address such challenges, the echo time can be reduced by using fractional motion encoding and/or mutli-shot EPI for each blade. Additionally or alternatively, field effects can be incorporated into the acquired signal model, such that they can be prospectively accounted for during reconstruction using a model-based iterative reconstruction ("MBIR"). For instance, this could be done either directly using an explicit field map model or indirectly using a so-called point spread function ("PSF") acquisition. In some aspects, the TURBINE-MRE pulse sequence may use a TR time that is an integer multiple of the motion period (e.g., 60 Hz or 80 Hz in the studies described in the present disclosure), a delay time may also be used after the sequence waveform, which may prolong the scan time. To reduce this delay time, an interleaved phase offsets acquisition can be incorporated into the sequence to further reduce scan time, in a non-limiting example.

Figure 4:
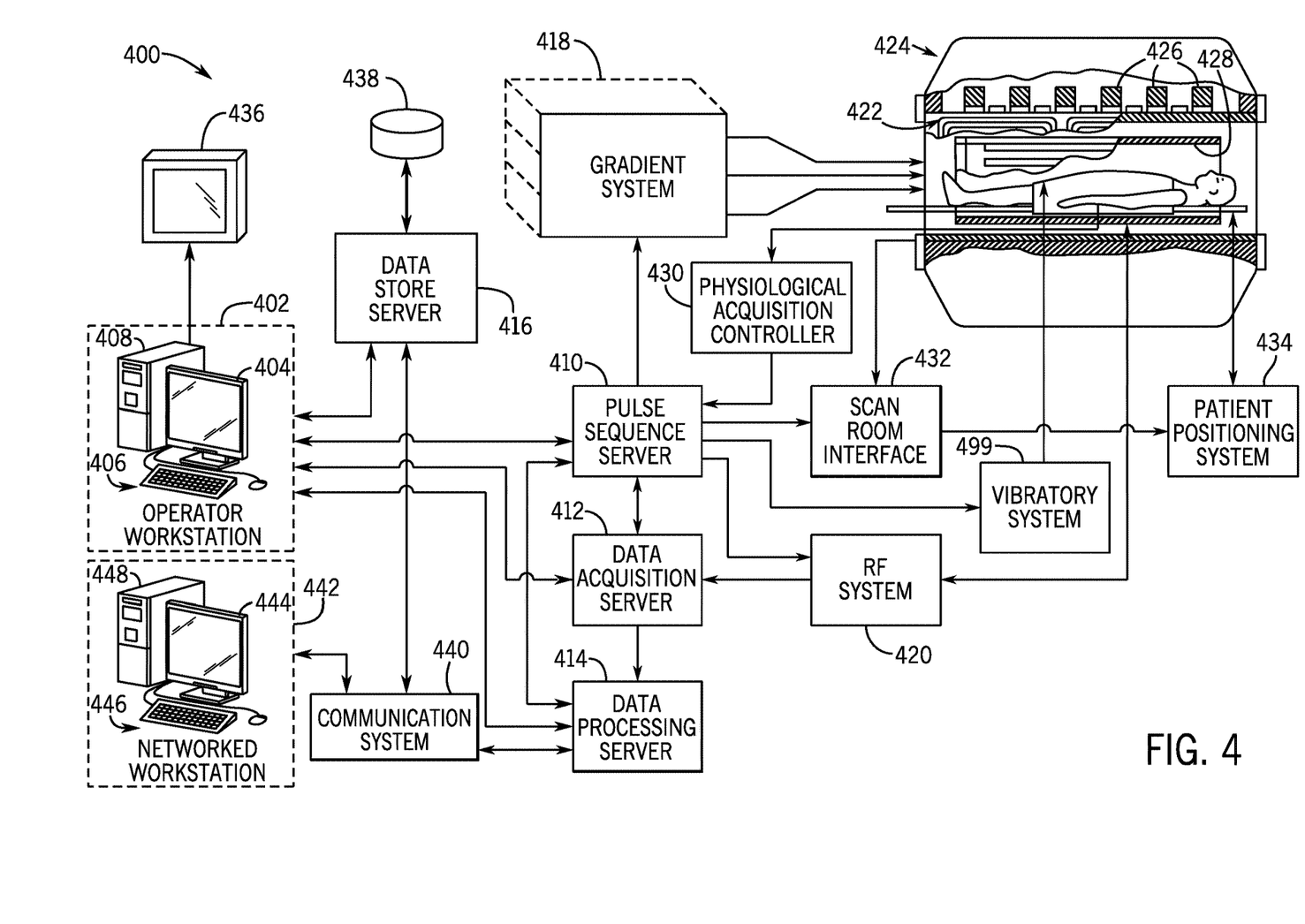
FIG. 4 is a block diagram of an example MRI system that can implement the methods described in the present disclosure.

Referring particularly now to FIG. 4, an example of an MRI system 400 that can implement the methods described here is illustrated. The MRI system 400 includes an operator workstation 402 that may include a display 404, one or more input devices 406 (e.g., a keyboard, a mouse), and a processor 408. The processor 408 may include a commercially available programmable machine running a commercially available operating system. The operator workstation 402 provides an operator interface that facilitates entering scan parameters into the MRI system 400. The operator workstation 402 may be coupled to different servers, including, for example, a pulse sequence server 410, a data acquisition server 412, a data processing server 414, and a data store server 416. The operator workstation 402 and the servers 410, 412, 414, and 416 may be connected via a communication system 440, which may include wired or wireless network connections. For performing MRE, a vibratory system 499 may be used to impart a vibration to a subject, such as with a pneumatic driver, which may be in communication with the MRI system 400.

The pulse sequence server 410 functions in response to instructions provided by the operator workstation 402 to operate a gradient system 418 and a radiofrequency ("RF") system 420. Gradient waveforms for performing a prescribed scan are produced and applied to the gradient system 418, which then excites gradient coils in an assembly 422 to produce the magnetic field gradients $G_x$, $G_y$, and $G_z$ that are used for spatially encoding magnetic resonance signals. The gradient coil assembly 422 forms part of a magnet assembly 424 that includes a polarizing magnet 426 and a whole-body RF coil 428.

RF waveforms are applied by the RF system 420 to the RF coil 428, or a separate local coil to perform the prescribed magnetic resonance pulse sequence. Responsive magnetic resonance signals detected by the RF coil 428, or a separate local coil, are received by the RF system 420. The responsive magnetic resonance signals may be amplified, demodulated, filtered, and digitized under direction of commands produced by the pulse sequence server 410. The RF system 420 includes an RF transmitter for producing a wide variety of RF pulses used in MRI pulse sequences. The RF transmitter is responsive to the prescribed scan and direction from the pulse sequence server 410 to produce RF pulses of the desired frequency, phase, and pulse amplitude waveform. The generated RF pulses may be applied to the whole-body RF coil 428 or to one or more local coils or coil arrays.

The RF system 420 also includes one or more RF receiver channels. An RF receiver channel includes an RF preamplifier that amplifies the magnetic resonance signal received by the coil 428 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \tag{1}$$

and the phase of the received magnetic resonance signal may also be determined according to the following relationship:

$$\varphi = \tan^{-1}\left(\frac{Q}{I}\right). \tag{2}$$

The pulse sequence server 410 may receive patient data from a physiological acquisition controller 430. By way of example, the physiological acquisition controller 430 may receive signals from a number of different sensors connected to the patient, including electrocardiograph ("ECG") signals from electrodes, or respiratory signals from a respiratory bellows or other respiratory monitoring devices. These signals may be used by the pulse sequence server 410 to synchronize, or "gate," the performance of the scan with the subject's heart beat or respiration.

The pulse sequence server 410 may also connect to a scan room interface circuit 432 that receives signals from various sensors associated with the condition of the patient and the magnet system. Through the scan room interface circuit 432, a patient positioning system 434 can receive commands to move the patient to desired positions during the scan.

The digitized magnetic resonance signal samples produced by the RF system 420 are received by the data acquisition server 412. The data acquisition server 412 operates in response to instructions downloaded from the operator workstation 402 to receive the real-time magnetic resonance data and provide buffer storage, so that data is not lost by data overrun. In some scans, the data acquisition server 412 passes the acquired magnetic resonance data to the data processor server 414. In scans that require information derived from acquired magnetic resonance data to control the further performance of the scan, the data acquisition server 412 may be programmed to produce such information and convey it to the pulse sequence server 410. For example, during pre-scans, magnetic resonance data may be acquired and used to calibrate the pulse sequence performed by the pulse sequence server 410. As another example, navigator signals may be acquired and used to adjust the operating parameters of the RF system 420 or the gradient system 418, or to control the view order in which k-space is sampled. In still another example, the data acquisition server 412 may also process magnetic resonance signals used to detect the arrival of a contrast agent in a magnetic resonance angiography ("MRA") scan. For example, the data acquisition server 412 may acquire magnetic resonance data and processes it in real-time to produce information that is used to control the scan.

The data processing server 414 receives magnetic resonance data from the data acquisition server 412 and processes the magnetic resonance data in accordance with instructions provided by the operator workstation 402. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 414 are conveyed back to the operator workstation 402 for storage. Real-time images may be stored in a data base memory cache, from which they may be output to operator display 402 or a display 436. Batch mode images or selected real time images may be stored in a host database on disc storage 438. When such images have been reconstructed and transferred to storage, the data processing server 414 may notify the data store server 416 on the operator workstation 402. The operator workstation 402 may be used by an operator to archive the images, produce films, or send the images via a network to other facilities.

The MRI system 400 may also include one or more networked workstations 442. For example, a networked workstation 442 may include a display 444, one or more input devices 446 (e.g., a keyboard, a mouse), and a processor 448. The networked workstation 442 may be located within the same facility as the operator workstation 402, or in a different facility, such as a different healthcare institution or clinic.

The networked workstation 442 may gain remote access to the data processing server 414 or data store server 416 via the communication system 440. Accordingly, multiple networked workstations 442 may have access to the data processing server 414 and the data store server 416. In this manner, magnetic resonance data, reconstructed images, or other data may be exchanged between the data processing server 414 or the data store server 416 and the networked workstations 442, such that the data or images may be remotely processed by a networked workstation 442.

Figure 5:
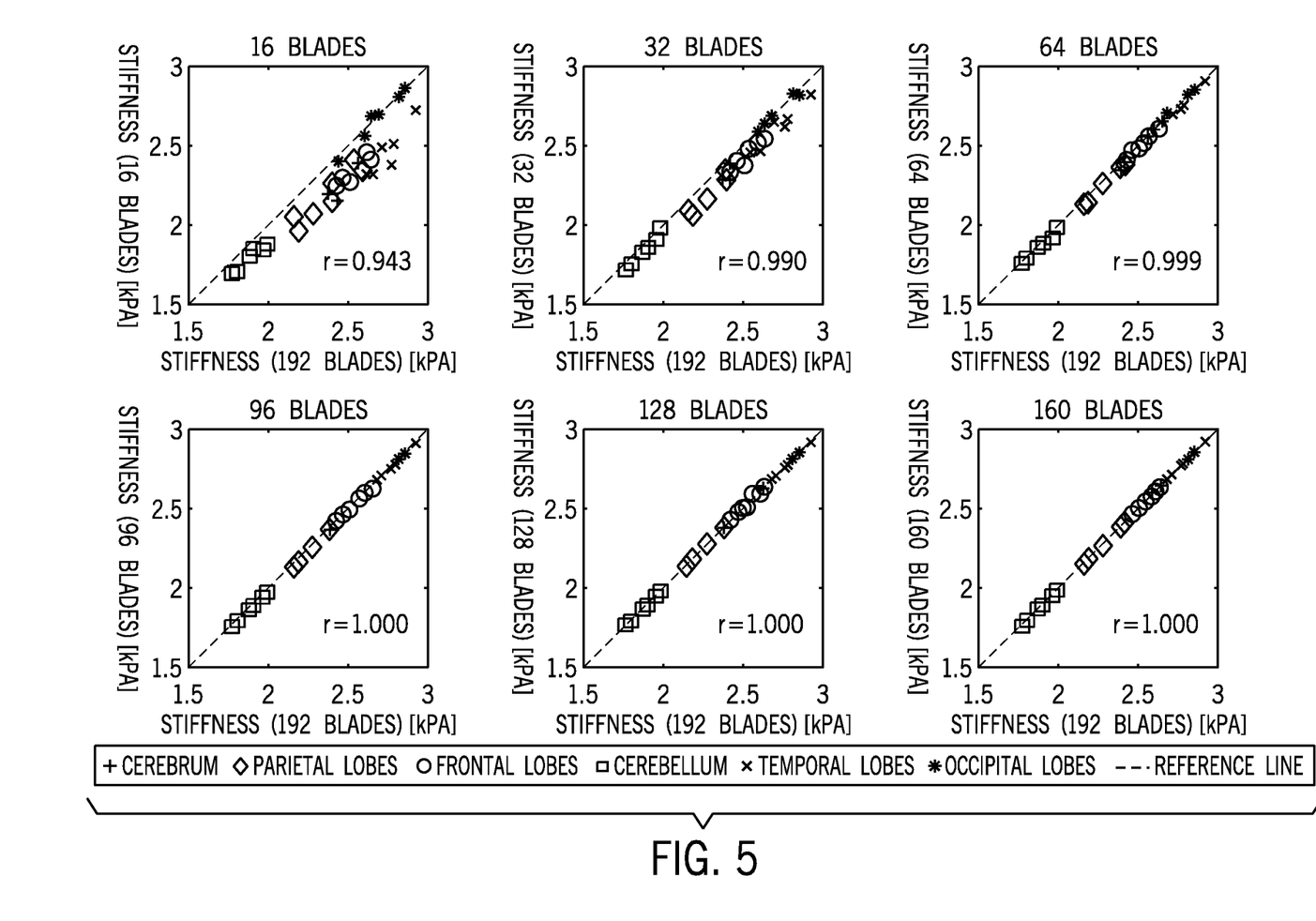
FIG. 5 is a set of scatter plots of non-limiting example stiffness data acquired in accordance with the present disclosure.

Referring to FIG. 5, scatter plots of non-limiting example stiffness data acquired in accordance with the methods of the present disclosure are shown. The scatter plots display median regional stiffness values when using different numbers of blades for reconstruction. As indicated, stiffness obtained with >=64 blades is almost identical to the one with 192 blades (r>=0.999) in the example. As articulated above, any number of blades may be used, and a user may select the number of blades used to optimize a balance between accuracy and computational resources.

The present disclosure has described one or more preferred embodiments, and it should be appreciated that many equivalents, alternatives, variations, and modifications, aside from those expressly stated, are possible and within the scope of the invention.

The invention claimed is:

1. A method for generating a mechanical property map using a magnetic resonance imaging (MRI) system, the method comprising:
   (a) acquiring data from a subject using the MRI system while a vibratory stimulus is provided to the subject in order to induce motion within a tissue of the subject, wherein:
      the data are acquired using a pulse sequence that samples k-space in a plurality of planes using an echo planar readout,
      each plane is radially rotated about a phase encoding axis in successive repetition time periods of the pulse sequence, and
      the pulse sequence includes motion encoding gradients that are generated before each echo planar readout in order to encode the motion within the tissue into an image phase of the data;
      wherein the data are acquired with uniform undersampling in a through-plane dimension;
   (b) reconstructing a plurality of images from the data using an iterative sparsity regularized image reconstruction technique based on a signal model that includes a forward operator that accounts for the uniform undersampling in the through-plane dimension, wherein the reconstructed images are indicative of the image phase into which the motion within the tissue has been encoded; and
   (c) generating a mechanical property map from the reconstructed images.

2. The method as recited in claim 1, wherein second data are acquired with the MRI system while the vibratory stimulus is provided to the subject, wherein the vibratory stimulus is triggered to be temporally shifted relative to the motion encoding gradients in the pulse sequence by a time delay such that the second data are acquired during a different phase of the motion within the tissue.

3. The method as recited in claim 1, wherein the iterative reconstruction implements an L1-regularization with a lifted Daubechies-4 wavelet transform.

4. The method as recited in claim 3, wherein the iterative reconstruction implements cycle spinning in a neighborhood.

5. The method as recited in claim 4, wherein the neighborhood is a 5 pixel by 5 pixel neighborhood.

6. The method as recited in claim 5, wherein the iterative image reconstruction is performed using a fast composite splitting algorithm.

7. The method as recited in claim 1, wherein each plane is radially rotated about the phase encoding axis in successive repetition time periods of the pulse sequence according to a uniform distribution of rotation angles over an angular range.

8. The method as recited in claim 7, wherein the angular range is 180 degrees.

9. The method as recited in claim 1, wherein each plane is radially rotated about the phase encoding axis in successive repetition time periods of the pulse sequence according to a golden angle increment.

10. The method as recited in claim 1, wherein an echo time of the pulse sequence is reduced using fractional motion encoding.

11. The method as recited in claim 1, wherein field effects are incorporated into a signal model used in the iterative image reconstruction such that the field effects are prospectively accounted for during reconstruction.

12. The method for generating a mechanical property map of claim 1, wherein the data are acquired with further undersampling in an in-plane dimension.

13. A magnetic resonance imaging (MRI) system for generating a mechanical property map of a subject, the system comprising:
(a) a vibratory stimulus system configured to induce motion within a tissue of the subject,
(b) a computer system configured to:
  (i) acquire data from the subject, while the induced motion is provided to the subject, using a pulse sequence that samples k-space in a plurality of planes using an echo planar readout;
  (ii) radially rotate each plane about a phase encoding axis in successive repetition time periods of the pulse sequence, wherein the pulse sequence includes motion encoding gradients that are generated before each echo planar readout in order to encode the motion within the tissue into an image phase of the data; and wherein the data are acquired with uniform undersampling in a through-plane dimension;
  (iii) reconstruct a plurality of images from the data using an iterative sparsity regularized image reconstruction technique based on a signal model that includes a forward operator that accounts for the uniform undersampling in the through-plane dimension, wherein the reconstructed images are indicative of the image phase into which the motion within the tissue has been encoded; and
  (iv) generate a mechanical property map from the reconstructed images.

* * * * *

UNITED STATES PATENT AND TRADEMARK OFFICE
CERTIFICATE OF CORRECTION

PATENT NO. : 12,130,348 B2
APPLICATION NO. : 17/793633
DATED : October 29, 2024
INVENTOR(S) : Arvin Forghanian-Arani et al.

Page 1 of 1

It is certified that error appears in the above-identified patent and that said Letters Patent is hereby corrected as shown below:

In the Specification

Column 3, Line 45, "Go" should be --$G_\theta$--.

Column 5, Line 29, "see" should be --sec--.

Signed and Sealed this
Thirty-first Day of December, 2024

Derrick Brent
*Acting Director of the United States Patent and Trademark Office*